Figure 1:
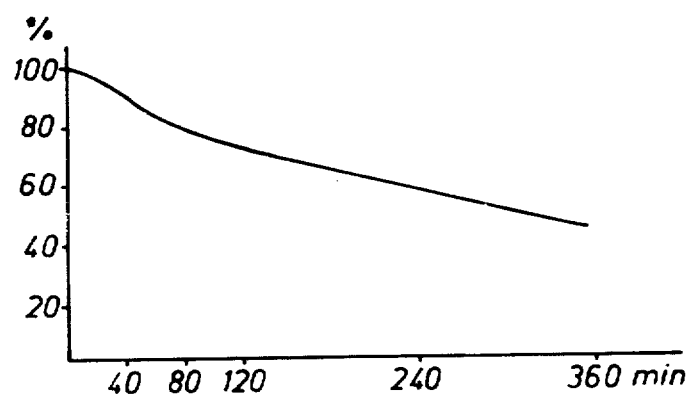

United States Patent [19]

Wedemeyer et al.

[11] 4,034,042
[45] July 5, 1977

[54] PROCESS FOR THE PRODUCTION OF 4-NITROSO-DIPHENYLAMINE

[75] Inventors: Karlfried Wedemeyer; Rudolf Helm, both of Cologne, Germany

[73] Assignee: Bayer Aktiengesellschaft, Germany

[22] Filed: Mar. 5, 1973

[21] Appl. No.: 338,219

[30] Foreign Application Priority Data
Mar. 9, 1972 Germany .................. 2211341

[52] U.S. Cl. .................................................. 260/576
[51] Int. Cl.² ......................................... C07C 87/28
[58] Field of Search ................................. 260/576

[56] References Cited

UNITED STATES PATENTS

| 3,429,924 | 2/1969 | Ellerbrook et al. | 260/576 |
| 3,728,392 | 4/1973 | Levy et al. | 260/576 |
| 3,748,362 | 7/1973 | Kinstler | 260/576 |

*Primary Examiner*—Elbert L. Roberts
*Attorney, Agent, or Firm*—Connolly and Hutz

[57] ABSTRACT

Object of the invention is a process for the production of 4-nitroso diphenylamine wherein N-nitroso diphenylamine is rearranged in the presence of an alcoholic hydrogen chloride solution by selecting the reaction conditions in such a way that the hydrochloride of 4-nitroso diphenylamine remains dissolved in the reaction medium. In this way spontaneous, uncontrollable decompositions do not occur.

6 Claims, 2 Drawing Figures

PROCESS FOR THE PRODUCTION OF 4-NITROSO-DIPHENYLAMINE

It is generally known that 4-nitroso diphenylamine can be produced by the re-arrangement of N-nitroso diphenylamine in the presence of alcoholic hydrochloric acid, the 4-nitroso diphenylamine accumulating in the form of its hydrochloride salt.

Spontaneous, uncontrollable decompositions occasionally occur when this process is carried out on an industrial scale. It is assumed that the 4-nitroso diphenylamine hydrochloride crystals are thermally unstable and that they decompose in the event of local overheating in the crystal paste which accumulates during the reaction. This local overheating always occurs if the intense heat of reaction is not uniformly dissipated to an adequate extent and it is additionally promoted by the ready tendency of the crystals to cake on the inner surfaces of the reaction vessel. The result of such decomposition, during which approximately 18 Kcal per mol of 4-nitroso diphenylamine hydrochloride are liberated and which progresses unchecked throughout the entire reaction mass, is that the vessel overfoams and nitrous gases and hydrogen chloride are liberated. The solvents are evaporated and a black, greasy residue is left in the vessel.

The re-arrangement of N-nitroso diphenylamine into the 4-nitroso compound has been varied in many respects. In most cases, precautions have to be taken to ensure the strict absence of water and moisture because otherwise the yield is seriously affected. One-stage processes have been described, for example in U.S. Pat. No. 2,046,356, according to which both the nitrosation of diphenylamine with sodium nitrite and also the subsequent re-arrangement by hydrogen chloride are carried out in absolute methanolic solution. However, this process gives a product having a low melting point. Also, the 4-nitroso diphenylamine hydrochloride accumulates in crystalline form. In U.S. Pat. No. 2,495,774, an attempt is made to obviate the difficulties involved in obtaining anhydrous conditions by adding acid chlorides which form hydrochloric acid by reaction with water. U.S. Pat. No. 2,782,235 relates to a process in which re-arrangement is carried out in an alcohol having more than 2 carbon atoms. In this case, it is even possible to use aqueous hydrochloric acid. Unfortunately, this procedure has considerable disadvantages. The yields are reduced, complicated purifying operations are necessary, recovery of the solvent is difficult and the conversion, based on the hydrogen chloride used, is extremely low. U.S. Pat. No. 3,429,924 attempts to obviate these disadvantages by carrying out the re-arrangement of N-nitroso diphenylamine in a lower alcohol, a fine suspension in the alcohol being obtained by pumping in the molten starting material. Although it is possible in this way to obtain extremely good yields, the 4-nitroso diphenylamine hydrochloride again accumulates in the form of a crystal paste. In addition the necessity for complicated working up, another disadvantage is the fact that isolated N-nitroso diphenylamine has to be used.

All these processes for the production of 4-nitroso diphenylamine are carried out on the batch principle with the object of obtaining the highest possible quantitative conversion. During the reactions just described, the 4-nitroso diphenylamine hydrochloride accumulates in crystalline form and gives rise to the disadvantages referred to above.

It has now been found that the spontaneous decomposition of 4-nitroso diphenylamine hydrochloride crystals can be avoided by ensuring that the hydrochloride formed during the reaction is not precipitated from the solution. Although a gradual decomposition of the hydrochloride begins at a much earilier stage when working in solutions, this disadvantage is accepted because there are no uncontrollable decompositions of the kind which occur when the hydrochloric crystals precipitate during the reaction.

The accompanying FIG. 1 illustrates the stability of 4-nitroso diphenylamine hydrochloride in methanol solution with the addition of hydrogen chloride, the molar ratio of 4-nitrosodiphenylamine to hydrogen chloride being 1 : 2, at a temperature of 40° C. It can be deduced from Table 1 of U.S. Pat. No. 3,429,924 that decomposition of the 4-nitroso diphenylamine hydrochloride suspensions begins at a later stage.

When working in solution, therefore, the reaction times have to be kept as short as possible on account of the earlier onset of decomposition. For a given solvent and at a given reaction temperature, the reaction velocity is governed both by the concentration of the N-nitroso diphenylamine and also by the concentration of hydrogen chloride. In order to obtain a short reaction time through a high reaction velocity, it is possible on the one hand, at a given reaction temperature, to increase the concentration of the hydrogen chloride, in which case the quantity of alcohol has to be adjusted so that the hydrochloride formed remains in solution. On the other hand, it is possible to increase the concentration of N-nitroso diphenylamine and deliberately to rearrange only a portion thereof, i.e. to carry out the reaction at a reduced conversion.

Accordingly, the present invention provides a process for the production of 4-nitroso diphenylamine from N-nitroso diphenylamine by re-arrangement in an alcoholic hydrogen chloride solution, optionally in admixture with an organic solvent that is immiscible with water, distinguished by the fact that the resulting 4-nitroso diphenylamine hydrochloride formed is prevented from crystallising out by selecting the reaction conditions in such a way that the hydrochloride of the 4-nitros diphenylamine remains dissolved in the reaction medium.

In cases where high concentrations of hydrogen chloride are used, high yields are obtained in short reaction time without any appreciable formation of secondary products. Suitable alcohols include linear, branched and alicyclic alcohols having from 1 to 10 carbon atoms, for example, methanol, ethanol, propanol, isopropanol, butanol, isobutanol, octanol, decanol and cyclohexanol, although it is preferred to use the lower alcohols of this series because the solubility of the hydrochloride is at its most favourable in these particular alcohols. The alcohols may optionally be used in admixture with an organic solvent which is immiscible with water. Suitable organic solvents include aromatic, optionally substituted hydrocarbons having from 6 to 8 carbon atoms for example, benzene, toluene, xylene, nitrobenzene or chlorobenzene, also chlorinated hydrocarbons having 1 or 2carbon atoms, for example, chloroform or carbon tetrachloride. However, the quantity in which the alcohol or solvent mixture is used must be adapted to the quantity of the 4-nitroso diphenylamine hydrochloride formed so that a solution is guaranteed, the lower limit being imposed by the solubility of the hydrochloride in the particular alcohol or solvent mixture. However, it is preferred to use a slight excess of the alcohol or solvent mixture which, on account of the drop in the concentrations of the reactants, cannot be indefinitely increased because otherwise the reaction velocity decreases.

Basically, there is no upper limit to the molar ratio of hydrogen chloride to N-nitroso diphenylamine, although limits are imposed by the need for economy because the excess hydrogen chloride has to be neutralised with an alkali, and by the salting-out effect of the hydrogen chloride. The lower limit is governed by the reaction time, the reaction temperature and the particular solvent used. It is preferred to use up to 20 mols of hydrogen chloride, more paticularly up to 10 mols of hydrogen chloride, per mole of N-nitroso diphenylamine. The hydrogen chloride content of the alcoholic solution or the solvent mixture is preferably within the range from 1 % by weight up to the value determined by its solubilty in the corresponding alcohol or in the mixture. The reaction time is up to 4 hours, preferably up to 2 hours, being governed by the reaction temperature and hydrogen chloride concentration used. The reaction temperature is in the range from 0° to 65° C and preferably in the range from 15° to 55° C. The higher the reaction temperature, the shorter the necessary reaction times for a given concentration of hydrogen chloride. Thus, reaction times of 30 minutes are sufficient, for example, at a reaction temperature of 40° C and with a ratio of hydrogen chloride to N-nitroso diphenylamine of 3 : 1 in the methanol/benzene mixture.

Working up is carried out either by neutralising or by introducing the reaction solution into excess alkali liquor because the 4-nitroso diphenylamine is soluble in alkalis in its oxime form. 4-nitroso diphenylamine can be recovered from the aqueous alkali solution by the addition of acid, optionally after the water-immiscible solvent has been separated. The 4-nitroso diphenylamine has a sharp melting point and is completely soluble in alkali. There is no need for further purification of the product.

However, the alkaline solution can also be directly reduced by conventional methods to form 4-amino diphenylamine.

In cases where it is desired to avoid high concentrations of hydrogen chloride when working in solution, it is necessary to use a high concentration of N-nitroso diphenylamine and to subject it only to partial re-arrangement.

Recovery of the non-rearranged fraction of the starting material which is necessitated by the reduction in conversion is achieved by adding an aqueous solution of alkali liquor on completion of re-arrangement and converting the non-rearranged starting material into a solvent immiscible with water which can also be an alcohol immiscible with water. It is best to add a corresponding solvent at the outset. The already mentioned aromatic, optionally substituted hydrocarbons and the chlorinated hydrocarbons are used as the water-immiscible solvents. Alcohols immiscible with water are alcohols having from 4 to 6 carbon atoms, for example, butanol, isobutanol and hexanol.

The non-re-arranged N-nitroso diphenylamine remains dissolved in these solvents, whilst the 4-nitroso diphenylamine soluble in alkali liquor in its oxime form can be extracted in the form of an alkali salt. The free 4-nitroso diphenylamine can be directly recovered by neutralising the alkaline solutions. However the alkaline salt solution can also be reduced by conventional methods to 4-amino diphenylamine.

The organic phase which still contains the non-rearranged fraction of N-nitroso diphenylamine, can be enriched with the quantity of diphenylamine required to restore the original concentration and reacted with quantities, based on diphenylamine, of dilute sulphuric acid and aqueous alkali nitrite solution. Thus, the diphenylamine can be substantially quantitatively nitrosated by known methods. It is thereby possible to obtain a solution with an original concentration of starting material which can be re-used for rearrangement with alcoholic hydrogen chloride solution. The aqueous phase is separated off and discarded.

This procedure is particularly suitable for continuous working. To this end, the individual stages described above are arranged sequentially as follows and the solutions circulated (The reference numerals cited in brackets refer to FIG. 2): nitrosation of diphenylamine into N-nitroso diphenylamine by conventional two-phase processes 7, phase separation 10, rearrangement of the organic phase with alcoholic hydrogen chloride solution to a certain conversion adjusted in dependence upon the test parameters, for example, reaction temperature, residence time and quantity of hydrogen chloride 2; alkalating the solution with aqueous sodium hydroxide 3, phase separation 5 and returning the organic phase to the nitrosation stage 7 where the initial concentration is restored by nitrosation following the addition of diphenylamine 6 in a quantity determined by the conversion.

The reference numerals 1,4,6,8 and 9 show storage vessels for alcoholic hydrogen chloride solution 1, aqueous alkali solution 4, diphenylamine 6, alkali nitrite solution 8 and dilute sulphuric acid 9. Numeral 11 refers to the outlet for alkaline solution of 4-nitroso diphenylamine and 12 for the outlet for effluent.

Figure 2:
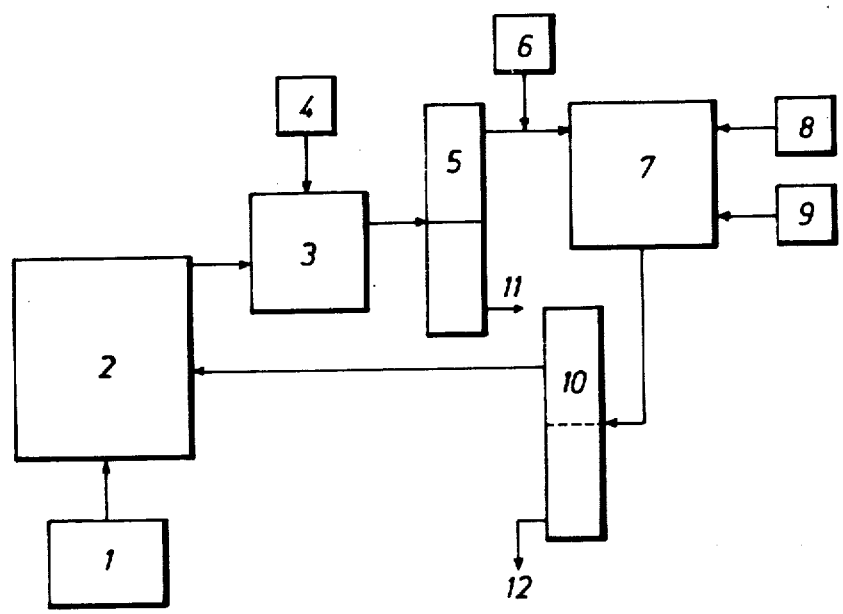

In order to illustrate the process, FIG. 2 digrammatically illustrates an apparatus for continuous operation. The reference numerals in the drawing have the following meaning:

1 = storage vessel for alcoholic hydrogen chloride solution
 2 = rearrangement apparatus
 3 = mixing vessel
 4 = storage vessel for aqueous alkali solution
 5 = phase separator
 6 = storage vessel for diphenylamine
 7 = nitrosation apparatus
 8 = storage vessel for alkali nitrite solution
 9 = storage vessel for dilute sulphuric acid
 10 = phase separator
 11 = alkaline solution of 4-nitroso diphenylamine
 12 = effluent However, the process according to the invention is by no means confined to the Figure.

Rearrangement is carried out at temperatures of from 0° to 65° C. preferably at temperatures of from 15° to 55° C. On account of the intense heat of reaction, it is necessary to effectively dissipate the heat, for example in an effectively coolable vessel, in a cascade of vessels, in a reaction tube or in a cyclic apparatus. Both in batch wise and continuous procedures, the N-nitroso diphenylamine dissolved in an organic solvent immiscible with water is mixed with an alcoholic hydrogen chloride solution (continuously) in such a way that the (average) residence time in the apparatus is up to 4 hours, preferably up to 2 hours. The hydrogen chloride content of the alcoholic solution of the solvent mixture is within the range from 1 % by weight up to the value determined by the solubility of the hydrogen chloride in the alcohol or solvent mixture. Up to 20 mols and preferably up to 10 mols of hydrogen chloride are used per mol of N-nitroso diphenylamine.

Subsequent (continous) alkalisation is carried out with at least that quantity of alkali which is required to neutralise the hydrogen chloride and to convert the 4-nitroso diphenylamine into its alkali salt. An excess of alkali is harmless and can even be advantageous in order to counteract hydrolysis. (Continuous) nitrosation of the diphenylamine added can be carried out at 15° to 17° C in a two-phase process by (continuously) adding dilute sulphuric acid and aqueous sodium nitrite solution.

If the reaction is carried out with partial conversion, the conversion can be varied within wide limits and can be fully controlled through the reaction parameters selected, for example, the reaction temperature, the residence time and the quantity of hydrogen chloride. The conversion may be between 5 and 95 % and preferably between 10 and 90 %. If a relatively high conversion is selected, it can also be decided to work up the residual quantity into starting material rather than to recycle it. If it is recycled, the total conversion is governed by the number of recycles.

For a conversion of 47 % for example, the total conversion amounts of 90 % with 10 recycles and to 93 % with 15 recycles. The number of recycles is governed solely by the quality-reducing enrichment level of the secondary products. These impurities can be eliminated both by completely removing and renewing the spent solutions at certain time intervals, and also by continuously removing the renewing a certain percentage of the solution. The spent solution can be treated for recovering the solvent and for working up unreacted N-nitroso diphenylamine.

The quality of the 4-nitroso diphenylamine formed is so high that the alkaline solution can be immediately delivered to the reduction stage or worked up by neutralisation into 4-nitroso diphenylamine. The alcohol used can also be recovered after reduction into 4-amino diphenylamine by a generally known method.

One of the advantages of the process according to the invention is that spontaneous decomposition is avoided, with the result that rearrangement takes place safely, even where the process is worked on a fairly large scale. Another advantage of the process is that it is eminently suitable for continuous working which produces a more effective dissipation of heat. Last but by no means least there is the advantage that the entire process can always be carried out in a liquid medium without any need to isolate intermediate stages.

4-nitroso diphenylamine is an important intermediate product for the production of antiagers for natural and/or synthetic rubber which can be obtained after reduction into 4-amino diphenylamine and alkylation, in each case by conventional methods.

The rearrangement according to the invention is illustrated in the following Examples. In the Example illustrating continuous working, all the quantitative references refer to the throughput per hour.

EXAMPLE 1

Solutions of 75 g of N-nitroso diphenylamine in 275 ml of benzene and of 60 g of hydrogen chloride in 230 g of methanol were run together into a reaction vessel equipped with a stirrer, an internal thermometer and two dropping funnels over a period of 10 minutes at a temperature kept at 40° C. Stirring was then continued for another 10 minutes at this temperature. The solution was then allowed to run with effective cooling into excess aqueous sodium hydroxide, the resulting mixture was thoroughly stirred and the phases were separated. The aqueous-alkaline phase was adjusted to pH 7–8, the deposit filtered off under suction, washed with water and dried. 4-nitroso diphenylamine (93 %) of m.p. 143°–144° C was obtained in a yield of 70 g (93 %), forming a yellow solution in acetone.

EXAMPLE 2

The procedure was as in Example 1, except that 40 g of HCl were used instead of 60 g and stirring was continued for 30 minutes instead of 10 minutes. 4-nitroso diphenylamine of m.p. 144°–145° C was obtained in a yield of 66.2 g (88 %), forming a yellow solution in acetone.

EXAMPLE 3

The procedure was as in Example 1, except that 80 g of HCl were used instead of 60 g and the reaction was carried out at 25° C instead of 40° C. 4-nitroso diphenylamine of m.p. 144°–145° C was obtained in a yield of 65.8 g (88%), forming a yellow solution in acetone.

EXAMPLE 4

The procedure was as in Example 1, except that only 40 g of HCl were used instead of 60 g. 4-nitroso diphenylamine of m.p. 142°–144° C was obtained in a yield of 64.9 g (86.5 %), forming a yellow solution in acetone. 55.5 g of diphenylamine were added to the benzene phase, followed by the addition of a solution of 33 g of concentrated sulphuric acid in 200 ml of water. A solution of 24.8 g of NaNo$_2$ in 180 ml of water was then added dropwise below the surface of the reaction mixture with thorough stirring at a temperature of 15°–17° C. Stirring was continued at the same temperature until the total reaction time amounted to 30 minutes. Following phase separation, the benzene phase was used as above for rearrangement, whilst the aqueous phase was discarded. After working up, 4-nitroso diphenylamine of m.p. 143°–144° C was obtained in a yield of 62 g (83 % of the theoretical field), forming a yellow solution in acetone.

EXAMPLE 5

A solution of 550 g of N-nitroso diphenylamine in 934 ml of benzene was prepared as a starting solution. The resulting solution, amounting to 1400 ml, was pumped continuously into a double-walled reaction vessel with a capacity of 410 ml. At the same time, a solution of 134 g of hydrogen chloride in 785 g of methanol (= 1060 ml), prepared with thorough cooling, was pumped in, again continuously. A temperature of 40° C was maintained by connecting a thermostat to the cooling system of the reaction vessel. The average residence time was 10 minutes. The solution leaving the rearrangement vessel was alkalated while stirring in a doublewalled mixing vessel cooled with cooling water by continuously introducing 200 g of NaOH in 1.5 liters of water (= 1.51 liters). The average residence time here was 30 minutes. The phase mixture is then continuously pumped over into a separator (1985 ml, average residence time 30 minutes), in which the phases were continuously separated. The benzene phase was enriched with 220 g of diphenylamine and delivered to the nitrosation apparatus. In the coolable and stirrable reaction vessel, the diphenylamine was subjected to nitrosation by the continuous introduction of 850 ml of dilute H$_2$SO$_4$ (130 g of concentrated H$_2$SO$_4$ and 800 ml of water) and 850 ml of NaNO$_2$-solution (97 g of NaNO$_2$ and 820 ml of water) at a temperature of 15° to 17° C. The residence time amounted to 30 minutes. The phase mixture leaving the nitrosation apparatus was separated in a continuous separator (average residence time: 30 minutes). The 1400 ml of benzene phase flowed continuously back into the rearrangement apparatus.

Normally, the aqueous-alkaline solution was directly hydrogenated into 4-amino diphenylamine. For controlling quality and conversion, the quantity accumulating over a period of 1 hour was worked up by adjusting the pH to a value of from 7 to 8 by the addition of HCl, the 4-nitroso diphenylamine precipitated was filtered off under suction, washed with water and then dried. 258 g (47 % conversion) were obtained, m.p. 142°–143° C. The substance was completely soluble in 35 % NaOH and gave a clear yellow solution in acetone.

What we claim is:

1. In the process of producing 4-nitrosodiphenylamine wherein N-nitrosodiphenylamine is subjected to rearrangement in an alcoholic hydrogen chloride solution and 4-nitrosodiphenylamine is recovered, the improved method of preventing spontaneous decomposition of 4-nitrosodiphenylamine hydrochloride which comprises regulating the ratio of hydrogen chloride to N-nitrosodiphenylamine in said solution, the rearrangement reaction temperature and the rearrangement reaction time in such a way that the resulting 4-nitrosodiphenylamine hydrochloride is prevented from crystallizing out and remains in solution during said rearrangement, and then neutralizing said 4-nitrosodiphenylamine hydrochloride and recovering resulting 4-nitrosodiphenylamine, there being up to 20 mols of hydrogen chloride used per mole of N-nitrosodiphenylamine reactant, said reaction temperature being in the range of from 0° to 65° C. and said reaction time being up to 4 hours.

2. The process of claim 1 wherein said alcoholic hydrogen chloride solution includes in admixture therewith an organic solvent which is immiscible in water.

3. The process of claim 1 wherein said process is carried out continuously.

4. The process of claim 1 wherein there are up to 10 mols of hydrogen chloride used per mol of N-nitrosodiphenylamine reactant.

5. The process of claim 1 wherein said reaction terperature is from 15° to 55° C.

6. The process of claim 1 wherein the conversion obtained in said rearrangement is from 5 to 95%.

* * * * *